United States Patent
Kunimi et al.

(10) Patent No.: US 8,991,260 B2
(45) Date of Patent: Mar. 31, 2015

(54) PSEUDO ROCK AND ANALYSIS SYSTEM USING THE SAME

(75) Inventors: Takashi Kunimi, Tokyo (JP); Shinichi Akutagawa, Kobe (JP)

(73) Assignee: Akebono Brake Industry Co., Ltd., Tokyo (JP)

( * ) Notice: Subject to any disclaimer, the term of this patent is extended or adjusted under 35 U.S.C. 154(b) by 116 days.

(21) Appl. No.: 13/814,058

(22) PCT Filed: Aug. 5, 2011

(86) PCT No.: PCT/JP2011/067960
§ 371 (c)(1),
(2), (4) Date: Feb. 4, 2013

(87) PCT Pub. No.: WO2012/018118
PCT Pub. Date: Feb. 9, 2012

(65) Prior Publication Data
US 2013/0125662 A1 May 23, 2013

(30) Foreign Application Priority Data
Aug. 5, 2010 (JP) .................................. 2010-176677

(51) Int. Cl.
G01V 1/00 (2006.01)
G01V 1/16 (2006.01)
G01N 33/24 (2006.01)
E21D 9/00 (2006.01)

(52) U.S. Cl.
CPC ................ *G01N 33/24* (2013.01); *E21D 9/003* (2013.01); *G01V 1/008* (2013.01); *G01V 1/166* (2013.01)

USPC .............................................. 73/645; 73/652

(58) Field of Classification Search
USPC .......................................................... 73/784
See application file for complete search history.

(56) References Cited

U.S. PATENT DOCUMENTS 4,492,111 A * 1/1985 Kirkland ........................... 73/84
6,791,901 B1 * 9/2004 Robertsson et al. ............. 367/58

FOREIGN PATENT DOCUMENTS

| JP | 60-263832 | 12/1985 |
|---|---|---|
| JP | 6-66950 | 3/1994 |
| JP | 9-251005 | 9/1997 |
| JP | 11-506540 | 6/1999 |
| JP | 2000-98046 | 4/2000 |
| JP | 2005-37313 | 2/2005 |
| JP | 2008-215913 | 9/2008 |

* cited by examiner

*Primary Examiner* — Harshad R Patel
(74) *Attorney, Agent, or Firm* — Drinker Biddle Reath LLP

(57) ABSTRACT

A pseudo rock includes a housing, a strain sensor, a three-axis acceleration sensor, a vibration generator and a controller. The housing has an average shape and size of rocks. The strain sensor detects a stress acting in positive and negative directions of each axis with respect to three-dimensional coordinates using the center of the housing as the origin. The three-axis acceleration sensor detects acceleration acting in each axis of the three-dimensional coordinates. The vibration generator produces vibration in a specific direction with respect to the three-dimensional coordinates. The controller converts respective detected values of the strain sensor and the three-axis acceleration sensor into vibration pulses of specific patterns and outputting the vibration pulses to the vibration generator.

9 Claims, 12 Drawing Sheets

DIRECTION OF GRAVITY G

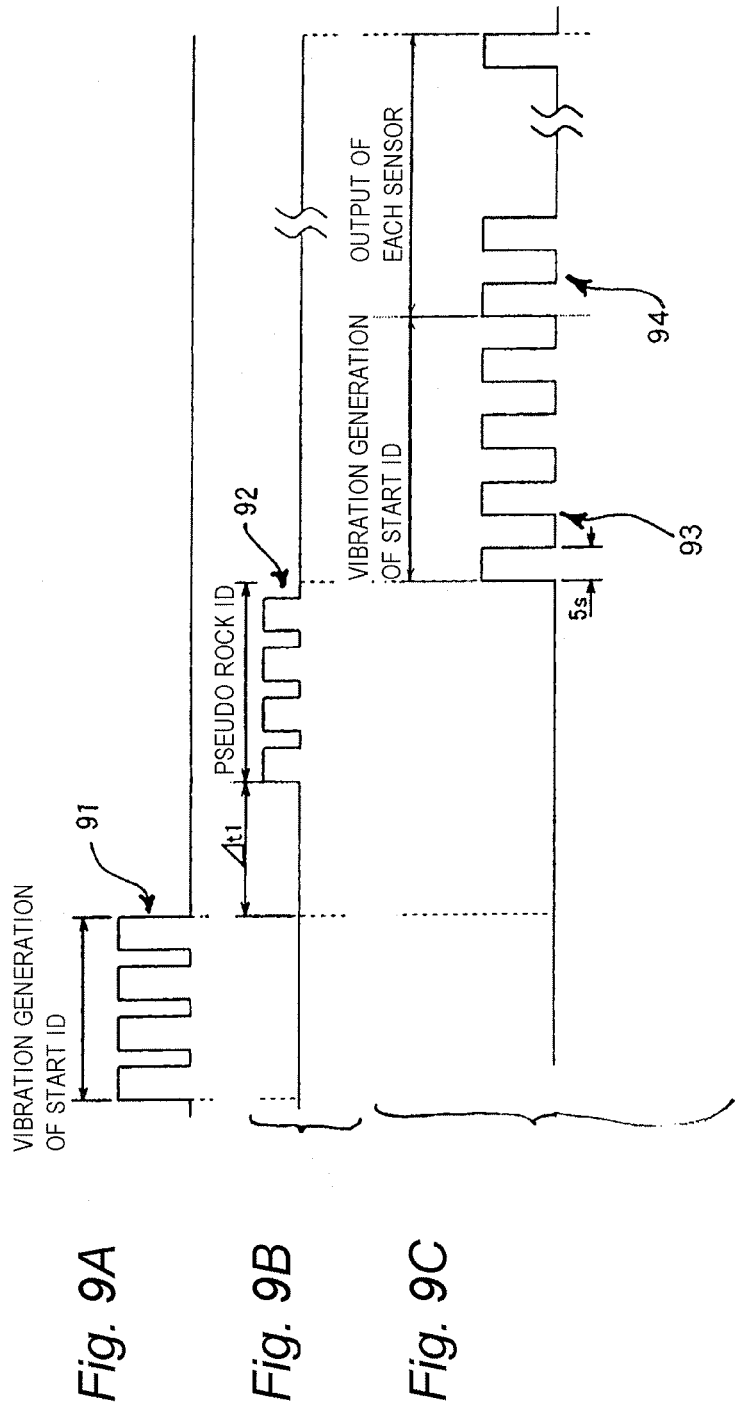

Fig. 10A
| START | ID | START | θZ | θX | θY | θHX | θHY | PX | PY | PZ | Temp | end |
|---|---|---|---|---|---|---|---|---|---|---|---|---|
| 1bit | 2bit | 1bit | 4bit | 4bit | 4bit | 4bit | 4bit | 4bit | 4bit | 4bit | 4bit | 2bit |
Fig. 10B
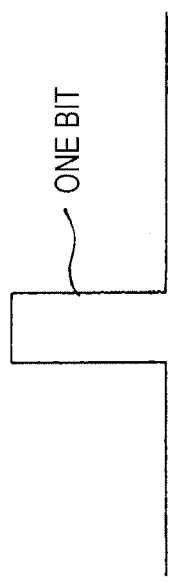
Fig. 10C
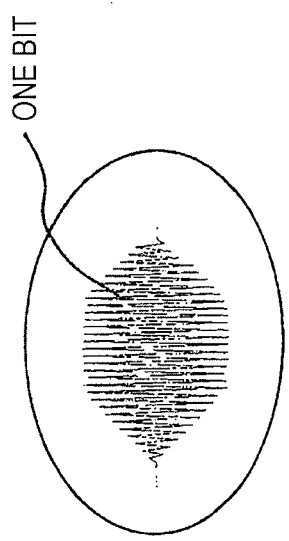

PSEUDO ROCK AND ANALYSIS SYSTEM USING THE SAME

TECHNICAL FIELD

The present invention is related to a pseudo rock for analyzing behavior of a rock at the time of collapse of a mineral deposit or the occurrence of a liquefaction phenomenon, and an analysis system using this pseudo rock.

BACKGROUND ART

Conventionally, a method (a block caving method) for widely cutting out a lower portion of a mineral deposit and collapsing the whole mineral deposit to a surface of the ground and picking ores out of the lower portion has received attention from an economic standpoint with deepening of the mineral deposit.

Conventionally, various devices or techniques have been proposed in order to detect and analyze an abnormality of the inside of a stratum, a mineral deposit or a tunnel. A technique for forming a pressure measurement probe installed in an artificial crack formed in an underground excavation borehole and monitoring displacement of a tunnel is disclosed in the following PTL 1. A technique for measuring displacement of a surface of a block of rock is disclosed in the following PTL 2. A technique for applying a magnetic field to a high-speed magnetic fluid injected into an investigation pit and analyzing an underground fracture structure is disclosed in the following PTL 3.

CITATION LIST

Patent Literature

[PTL 1] JP-A-2005-37313
[PTL 2] JP-A-11-506540
[PTL 3] JP-A-6-66950

SUMMARY OF INVENTION

Technical Problem

According to the prior art references described above, for example, the tunnel can be analyzed or displacement of the surface of the block of rock can be measured. On the contrary, in the block caving method, a situation in which collapse is caused while showing any behavior when any stress is applied to a rock of the inside of a mineral deposit obtains a very important parameter for simulating the start of the collapse or magnitude of the collapse.

On the other hand, when a huge earthquake occurs, there is fear that the so-called liquefaction phenomenon occurs in reclaimed ground etc. For analyzing a mechanism of the occurrence of such a liquefaction phenomenon, analysis of behavior of rocks constructing the ground obtains basic data in taking effective disaster-prevention measures.

Hence, in order to solve the problems described above, an object of the invention is to obtain accurate basic data for simulating the start of collapse, magnitude of the collapse or a mechanism of the occurrence of a liquefaction phenomenon by arranging a pseudo rock having an average shape and size (an average shape and size at the time of mining in a mineral deposit) constructing the mineral deposit or ground inside the mineral deposit or the ground and measuring a stress acting on the rock and behavior of the rock associated with the stress at the time of the collapse or the occurrence of the liquefaction phenomenon and collecting and analyzing the stress and the behavior.

Solution to Problem

In order to achieve this objective, the following technical measures are taken in a pseudo rock buried inside a mineral deposit or ground of the invention.

(1) The invention provides a pseudo rock comprising:
a housing having an average shape and size of rocks existing inside the mineral deposit or the ground;
a strain sensor configured to detect a stress acting in positive and negative directions of each axis with respect to three-dimensional coordinates (X axis, Y axis, Z axis) using the center of the housing as the origin;
a three-axis acceleration sensor configured to detect acceleration acting in each axis of the three-dimensional coordinates;
a vibration generator configured to produce vibration in a specific direction with respect to the three-dimensional coordinates; and
a controller configured to convert respective detected values of the strain sensor and the three-axis acceleration sensor into vibration pulses of specific patterns and outputting the vibration pulses to the vibration generator.

(2) An ID vibration pulse is individually allocated to the pseudo rock, and the controller outputs the vibration pulses of the specific patterns corresponding to the detected values by the strain sensor and the three-axis acceleration sensor together with the ID vibration pulse to the vibration generator.

(3) The controller includes power source controller configured to turn on an own power source when the three-axis acceleration sensor or a vibration sensor individually provided detects vibration of the ID vibration pulse.

(4) The pseudo rock further comprises a three-axis geomagnetic sensor.

(5) The invention provides a ground control apparatus configured to control the pseudo rock according to the present invention on ground, comprising:
a sending vibrator configured to send an ID vibration pulse of the pseudo rock to the pseudo rock to trigger the pseudo rock; and
a receiving sensor configured to detect vibration from a vibration generator of the pseudo rock.

(6) The receiving sensor detects a vibration pulse corresponding to detected values of the strain sensor and the three-axis acceleration sensor together with vibration corresponding to an ID vibration pulse of the pseudo rock from the pseudo rock, and the ground control apparatus further comprises a data analyzer configured to analyze each of the detected values of the strain sensor and the three-axis acceleration sensor of the pseudo rock together with the ID vibration pulse of the pseudo rock.

(7) The receiving sensor is arranged in at least three places of an outer periphery of the mineral deposit or the ground, and the ground control apparatus further comprises a position analyzer configured to analyze a three-dimensional position of the pseudo rock inside the mineral deposit or the ground based on a difference between arrival times of signals from a vibration generator of the pseudo rock.

(8) The ground control apparatus further comprises a three-dimensional coordinate analyzer configured to analyze an angle of inclination in a horizontal direction or an angle of inclination to a vertical direction of three-dimensional coordinates (X axis, Y axis, Z axis) of the pseudo rock based on a detected value of each of the strain sensors or the three-axis geomagnetic sensors of the pseudo rock.

(9) The invention provides a rock behavior analysis system, configured to analyze a rock inside of a mineral deposit or under ground, comprising the pseudo rock according to the (1) to (4) above and the ground control apparatus according to the (5) to (8) above.

Advantageous Effects of Invention

According to the pseudo rock of the invention, by the housing having a typical shape and size of rocks exist inside the mineral deposit or the ground, an average value of stresses or pressures to which the rocks present inside the mineral deposit or the ground are subjected from other rocks etc. can accurately be measured by the strain sensor etc. And further, vibration-based communication with the ground side can be established by the three-axis acceleration sensor for detecting acceleration acting in each axial direction of the three-dimensional coordinates and the vibration generator for producing vibration in the specific direction. Therefore, accurate basic data for simulating the start of collapse, magnitude of the collapse or a mechanism of the occurrence of a liquefaction phenomenon while pinpointing directions of the pressures or the stresses can be obtained.

Also, according to the ground control apparatus of the invention, by including the sending vibrator for triggering the pseudo rock described above and the receiving sensor for detecting vibration from the vibration generator of the pseudo rock, vibration-based communication with the pseudo rock can be conducted and activation of the pseudo rock or detected data obtained can accurately be received on the ground.

Further, according to the rock behavior analysis system of the invention, by combining the pseudo rock with the ground control apparatus described above, a measuring system for accurately measuring rock behavior can be constructed in a predetermined place of the mineral deposit or the ground.

BRIEF DESCRIPTION OF DRAWINGS

FIG. 9A shows four vibration pulses delivered by the sending vibrator of the ground control apparatus. FIG. 9B shows vibration pulses which a pseudo rock pinpointed by the four vibration pulses delivered by the sending vibrator of plural pseudo rocks detects by its own three-axis acceleration sensor. FIG. 9C shows its own ID vibration pulse which the pinpointed pseudo rock sequentially sends to the ground control apparatus by its own vibration generator, and vibration pulses subsequent to the ID vibration pulse, corresponding to detected values of the three-axis acceleration sensor, the three-axis geomagnetic sensor, a temperature sensor and each of the strain gauges.

FIG. 10A shows a data stream at the time when the pseudo rock sends an ID vibration pulse and a detected value of each sensor to the ground control apparatus by the vibration generator. FIG. 10B shows one bit by vibration used in the invention. FIG. 10C shows a configuration of the one bit by vibration.

DESCRIPTION OF EMBODIMENTS

An embodiment in the case of applying the invention to analysis of behavior of a rock at the time of collapse of a mineral deposit will hereinafter be described along with the drawings.

The present embodiment is an analysis system of behavior of a rock at the time of collapse of a mineral deposit, so that a pseudo rock used is set in an average size and shape in the case of being taken out of the mineral deposit, and is not particularly aware of an installation position, a direction, etc., and is installed in a state suitable to measure the behavior of the rock of the inside of the mineral deposit at the time of collapse.

Figure 1A:
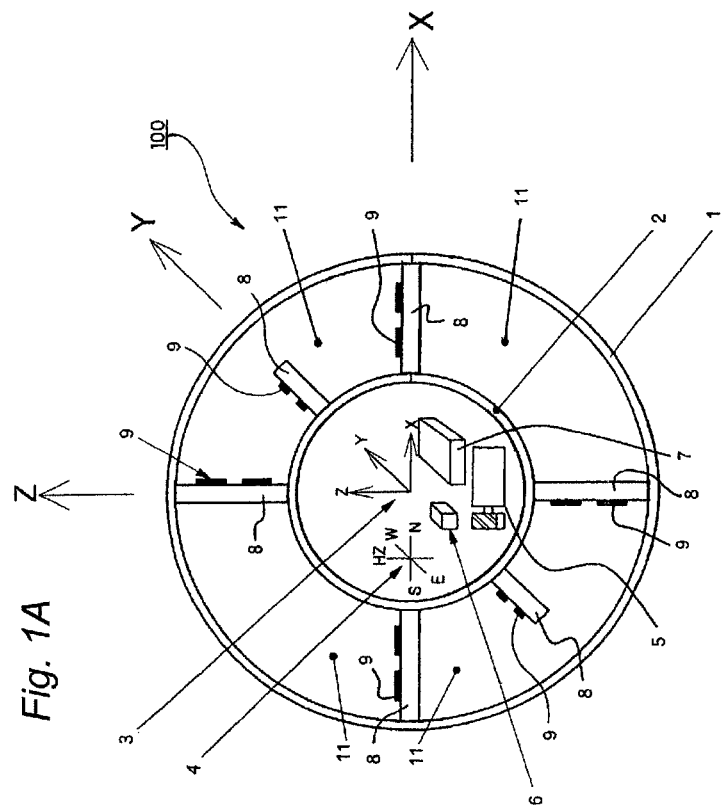
FIG. 1A is a diagram showing a structure of a pseudo rock according to the invention.

FIG. 1A shows a structure of a pseudo rock according to the embodiment.

In FIG. 1A, numeral 100 is a pseudo rock according to the embodiment. A housing of the pseudo rock 100 has a double structure of an outer shell sphere (pressure outer wall) 1 and an inner shell sphere 2, and the outer shell sphere (pressure outer wall) 1 is molded of, for example, iron or stainless steel, and has the strength capable of withstanding pressure applied from the rock inside a mineral deposit. A three-axis acceleration sensor 3, a three-axis geomagnetic sensor 4, a vibration generator (vibrator) 5, a temperature sensor 6 and an electric control unit (hereinafter called an ECU) 7 are housed inside the inner shell sphere 2.

The outer shell sphere 1 and the inner shell sphere 2 are coupled by six columnar members 8 extending in both positive and negative directions of X, Y, Z axes of the pseudo rock 100, and two strain gauges 9 which are strain sensors are respectively attached to this columnar member 8, and space of a battery such as a secondary battery is obtained using space 11 between the outer shell sphere 1 and the inner shell sphere 2.

In addition, the three-axis geomagnetic sensor 4 is used in the case of measuring an angle of inclination to the N axis in a horizontal plane of the pseudo rock 100 as described below, and is not required in the case of measuring only an angle of inclination to a vertical direction (a gravity action direction). Also, when the three-axis geomagnetic sensor 4 is used, it is necessary to use a geomagnetism transmitting material such as stainless steel as the outer shell sphere 1 so that geomagnetism can accurately be measured inside the pseudo rock 100.

In addition, in this embodiment, the housing of the pseudo rock 100 is formed in a spherical body of the double structure made of the outer shell sphere 1 and the inner shell sphere 2, but could be a cube, a rectangular parallelepiped or a solid shape having parallel opposed surfaces, and could properly be set according to an average shape etc. of rocks distributed inside a mineral deposit.

The strain gauge 9 measures a pressure or a shock acting on the outer shell sphere 1 due to contact, collision, etc. with other rocks of the inside of the mineral deposit before or after the start of collapse by strain of each of the columnar members 8 associated with the pressure or the shock, and can detect such a pressure or a shock with high accuracy in directions of six axes of both positive and negative directions of X, Y, Z axes of the pseudo rock 100.

In addition, this pseudo rock 100 is installed in at least one proper place inside the mineral deposit or the ground, but when the plural pseudo rocks 100 are arranged, higher-accuracy data can be collected in the case of analyzing a collapse phenomenon.

The vibration generator 5 produces vibration in a predetermined direction by rotating an eccentric weight as used in, for example, a mobile telephone at high speed by a motor, and this vibration is detected by the three-axis acceleration sensor 3, and vibrations in the directions of X, Y, Z axes of the pseudo rock 100 are detected. In addition, the vibration generator 5 is not limited to such a type of vibration generator, and any electric vibration generator such as a vibration generator using a coil may be adopted.

Incidentally, the pseudo rock 100 (FIG. 1A) is installed and buried at the initial value in a proper direction inside the mineral deposit, and also rotates in various directions by pressure applied from the peripheral rocks inside the mineral deposit. Therefore, the X, Y, Z axes of the pseudo rock 100 are inclined to global coordinates of the east-west direction, the north-south direction and the vertical direction (gravity action direction) on a surface of the ground in the various directions.

In the case of analyzing collapse, it is particularly necessary to determine a direction in which a pressure or a shock occurs when viewed from the vertical direction of the global coordinates with respect to the pseudo rock 100.

Figure 2:
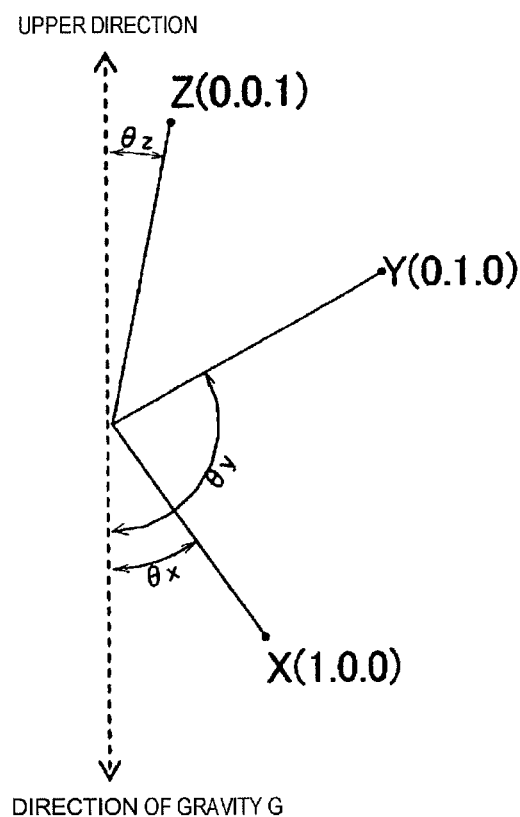
FIG. 2 is a diagram showing a principle for measuring an angle of inclination to a vertical direction of the pseudo rock by a three-axis acceleration sensor.

Here, as shown in FIG. 2, the X, Y, Z axes of the pseudo rock 100 (FIG. 1A) shall be inclined to the vertical direction at θx, θy, θz, respectively.

When acceleration vectors obtained based on an X-axis sensor output (Vx), a Y-axis sensor output (Vy) and a Z-axis sensor output (Vz) of the three-axis acceleration sensor 3 are set at (Vx, Vy, Vz) and unit vectors in the X, Y, Z axes of the pseudo rock 100 of vibration by the vibration generator 5 are set at (a, b, c), gravity acceleration VG acts on the horizontal plane in the vertical direction in the acceleration vectors, so that the unit vectors can be expressed as the following formulas from a relation between an Euler angle and a direction cosine matrix.

$X \text{ axis}(a.b.c)(1.0.0)=\cos \theta x = Vx/VG$ $Y \text{ axis}(a.b.c)(0.1.0)=\cos \theta y = Vy/VG$ $Z \text{ axis}(a.b.c)(0.0.1)=\cos \theta z = Vz/VG$ Therefore, θx, θy, θz can be obtained by phase analysis based on the X-axis sensor output (Vx), the Y-axis sensor output (Vy) and the Z-axis sensor output (Vz) by using the relational formulas.

It can be accurately analyzed a direction in which a pressure, a shock, etc. which act on the outer shell sphere 1 from the rock of the inside of the mineral deposit and are detected by each of the strain gauges 9 act with respect to the vertical direction of the global coordinates.

The three-axis geomagnetic sensor 4 is used in the case of pinpointing an angle of inclination to the horizontal direction as well as the vertical direction of the global coordinates.

Figure 3:
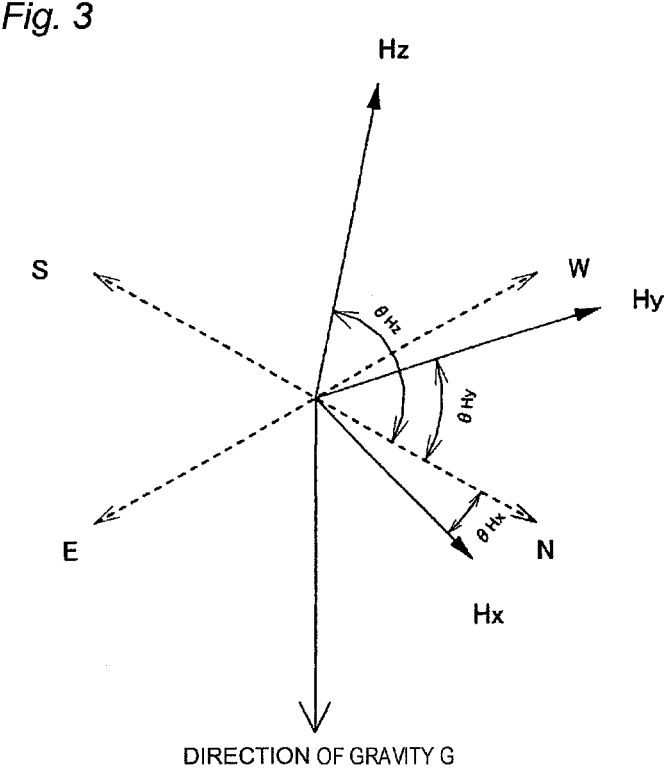
FIG. 3 is a diagram showing a principle for measuring an angle of inclination to a horizontal direction of the pseudo rock by a three-axis geomagnetic sensor.

This three-axis geomagnetic sensor 4 is means for detecting a direction component of geomagnetism acting in the N-S direction in the horizontal plane with respect to the X, Y, Z axes of the pseudo rock 100 (FIG. 1A) as shown in FIG. 3, and when geomagnetic sensor outputs in the directions of the X, Y, Z axes are respectively set at VHX, VHY, VHZ and an earth axis sensor output in the case of being installed in a direction of the North pole is set at VH and unit directional vectors of geomagnetism are set at (A, B, C), the vectors can be expressed as the following formulas similarly to pinpointing in the vertical direction.

$X \text{ axis}(A.B.C)(1.0.0)=\cos \theta HX = VHX/VH$ $Y \text{ axis}(A.B.C)(0.1.0)=\cos \theta HY = VHY/VH$ $Z \text{ axis}(A.B.C)(0.0.1)=\cos \theta HZ = VHZ/VH$ Therefore, θHX, θHY, θHZ can be obtained by phase analysis based on VH and VHX, VHY, VHZ by using the relational formulas when it is necessary to pinpoint an angle of inclination to the N-S direction of the pseudo rock 100.

It can be analyzed a direction in which a pressure, a shock, etc. which act on the outer shell sphere 1 from the rock of the inside of the mineral deposit and are detected by each of the strain gauges 9 act with respect to the NS direction.

Returning to FIG. 1A, electric power is supplied from a battery 44 (FIG. 4) housed in the battery space 11 to the ECU 7 stored inside the inner shell sphere 2 of the pseudo rock 100, and the three-axis acceleration sensor 3, the three-axis geomagnetic sensor 4, the temperature sensor 6 and each of the strain gauges 9 are connected to a CPU 43 of the ECU 7 through an input-output interface (not shown). The CPU 43 performs on-off control of a voltage of a base 48B of a transistor 48 and thereby, the motor constructing the vibration generator 5 rotates.

When the ECU 7 receives a starting vibration from a sending vibrator 10 installed in a ground control apparatus 200 (FIG. 7) described below, the ECU 7 responds to that starting vibration and converts each detected value of each of the acceleration sensors 3 into a corresponding frequency and actuates the vibration generator 5. And the ECU 7 generates the detected value to the ground control apparatus 200 or stores the detected value of each of the acceleration sensors 3 together with detection time in memory 42 (FIG. 4) as time-series data.

Figure 4:
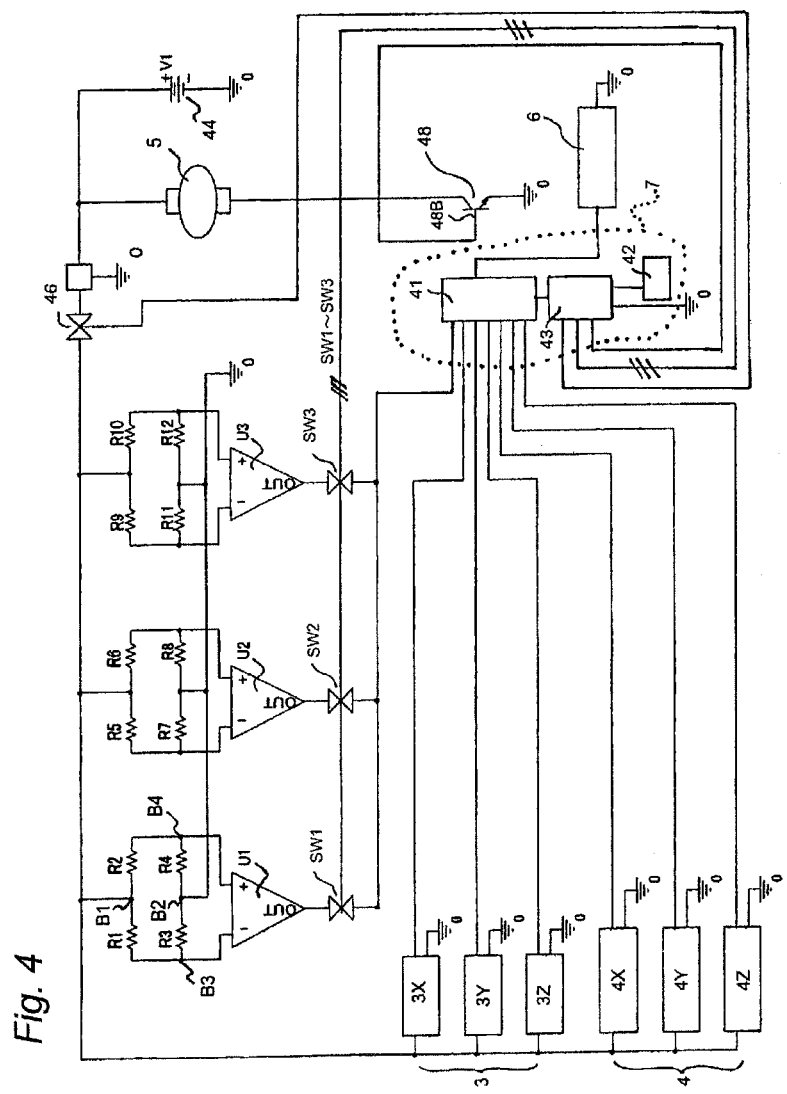
FIG. 4 is a block diagram showing a circuit connection configuration of the inside of the pseudo rock.

FIG. 4 shows a block diagram of the inside of the pseudo rock 100.

R1 and R2 of an upper stage show resistance values of the strain gauge 9 attached to the columnar member extending in a positive direction of the X axis, and R3 and R4 show resistance values of the strain gauge attached to the columnar member extending in a negative direction of the X axis. A bridge is formed by a series circuit of the resistance values R1 and R2 and a series circuit of the resistance values R3 and R4. A positive voltage of the battery 44 is applied to a point B1 of connection between the resistance values R1 and R2. An earth potential is applied to a point B2 of connection between the resistance values R3 and R4. A point B3 of connection between the resistance values R1 and R3 is connected to a first input terminal (minus terminal) of a differential amplifier U1. A point B4 of connection between the resistance values R4 and R2 is connected to a second input terminal (plus terminal) of the differential amplifier U1. Thereby, a change in each of the resistance values R1 to R4 associated with strain is outputted from an output terminal (OUT terminal) of the differential amplifier U1. This detected value is inputted to the CPU (central processing unit) 43 through an analog-to-digital (A/D) converter 41, and the CPU 43 can detect that any stress occurs in the positive direction (tensile direction) or the negative direction (compression direction) of the X axis. SW1 to SW3 are switches controlled by the CPU 43, and when SW1 is turned on and SW2 and SW3 are turned off, an output of the differential amplifier U1 is selected and is read in the A/D converter 41. By similar operation, three channels of the differential amplifiers U1 to U3 can be read by an A/D input of one channel. Since a semiconductor of A/D generally has an eight-channel input, the three channels are read by the A/D input of one channel in this manner.

Figure 1B:
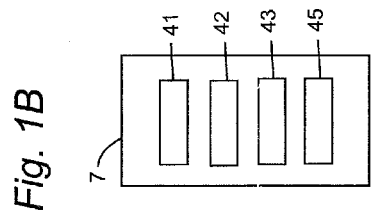
FIG. 1B is a block diagram showing an electric control unit.

The memory 42 is connected to the CPU 43. The A/D converter 41, the memory 42 and the CPU 43 are attached on one substrate to construct the ECU 7 (FIGS. 1A and 1B).

The same applies to R5 to R8 and R9 to R12. That is, R5 to R8 show resistance values of the strain gauge 9 attached to the columnar member 8 (FIG. 1A) extending in a positive direction (R5 and R6) and a negative direction (R7 and R8) of the Y axis and also, R9 to R12 show resistance values of the strain gauge 9 attached to the columnar member 8 extending in a positive direction (R9 and R10) and a negative direction (R11 and R12) of the Z axis, and the CPU 43 detects that any stress occurs in the positive direction or the negative direction of the Y axis, and in the positive direction or the negative direction of the Z axis, respectively.

Acceleration sensors 3X, 3Y, 3Z indicate the three-axis acceleration sensor 3. Then, geomagnetic sensors 4X, 4Y, 4Z indicate the three-axis geomagnetic sensor 4. In the three-axis acceleration sensor 3, the three-axis geomagnetic sensor 4 and the temperature sensor 6, these detected values are inputted to the CPU 43 constructing the ECU 7 through the A/D converter 41. Then, the CPU 43 performs on-off control of the motor of the vibration generator 5 by controlling the base voltage 48B of the transistor 48. Numeral 44 is a battery. Numeral 46 is a switch for turning on and off a power source for supply to each of the sensors, and the switch is controlled by a power source controller 45 of the ECU 7 (CPU 43). This switch 46 is turned off during standby, and power consumption of a system is reduced to increase the life of an internal battery. Also, as described above, in the case of receiving an ID vibration pulse from the ground control apparatus 200, the switch is turned on by the power source controller 45 of the ECU 7 (CPU 43) and each of the sensors is activated to start measurement.

Figure 5:
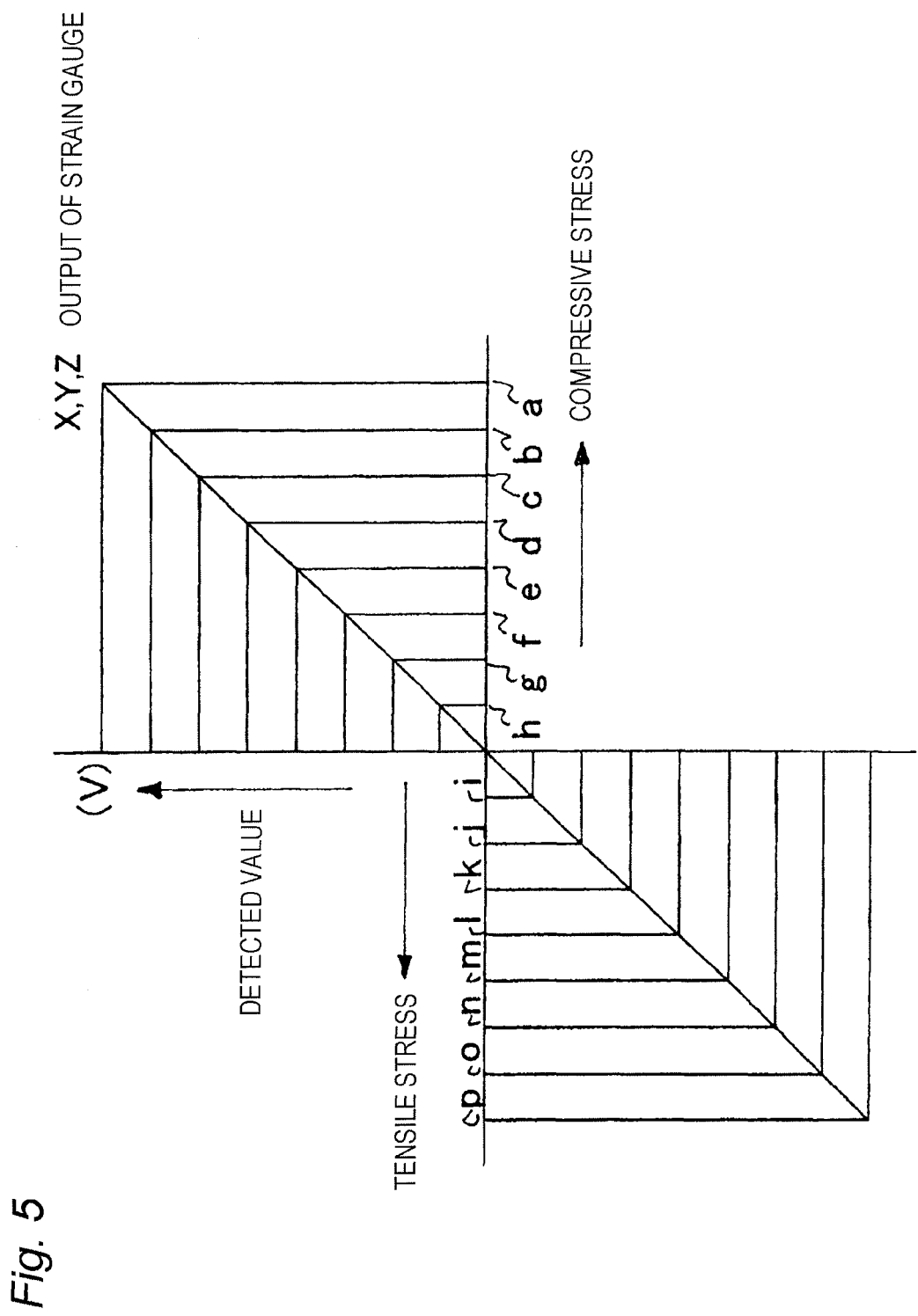
FIG. 5 is a diagram showing a relation between a detected value and a stress of a strain gauge.

FIG. 5 is a diagram showing a relation between a detected value (ordinate axis) and a stress (abscissa axis) of the strain gauge 9 (FIG. 1A). FIG. 5 shows that when a compressive stress (positive direction) or a tensile stress (negative direction) in the directions of the X, Y, Z axes is applied to the strain gauge 9, the detected value (voltage) of the differential amplifier U1 (FIG. 4) is outputted in proportion to that stress.

Figure 6:
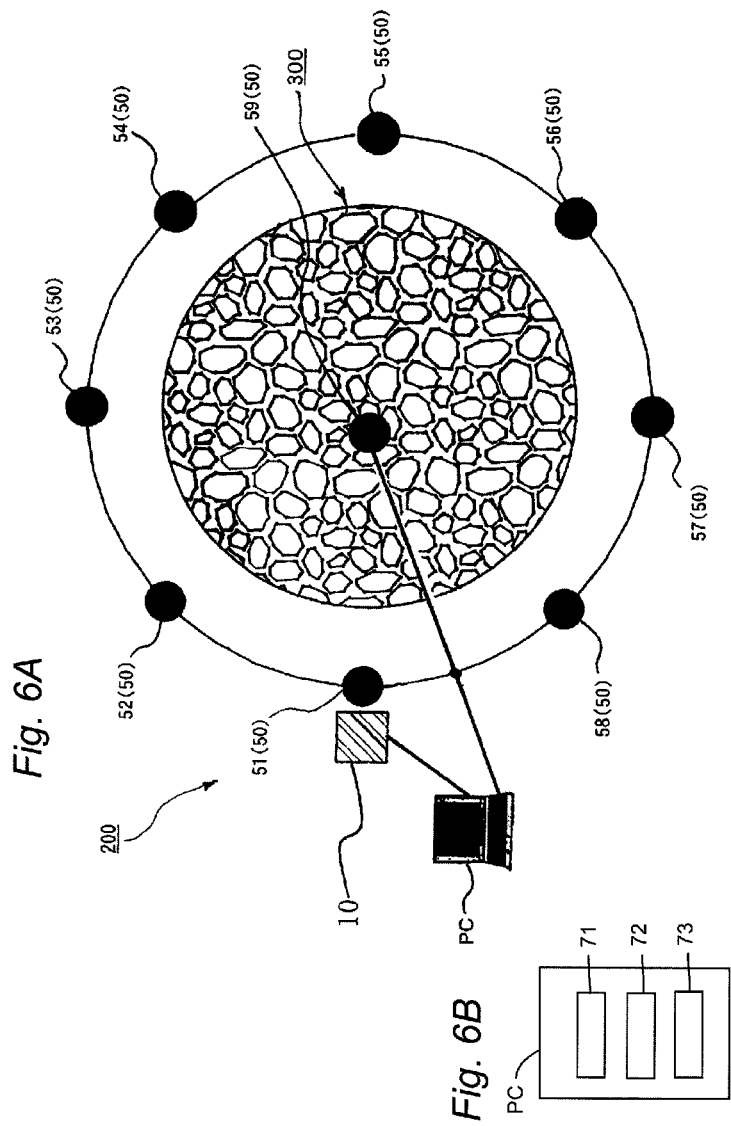
FIG. 6A is a plan view of a basic configuration of a ground control apparatus.
FIG. 6B is a block diagram showing a PC.
Figure 7:
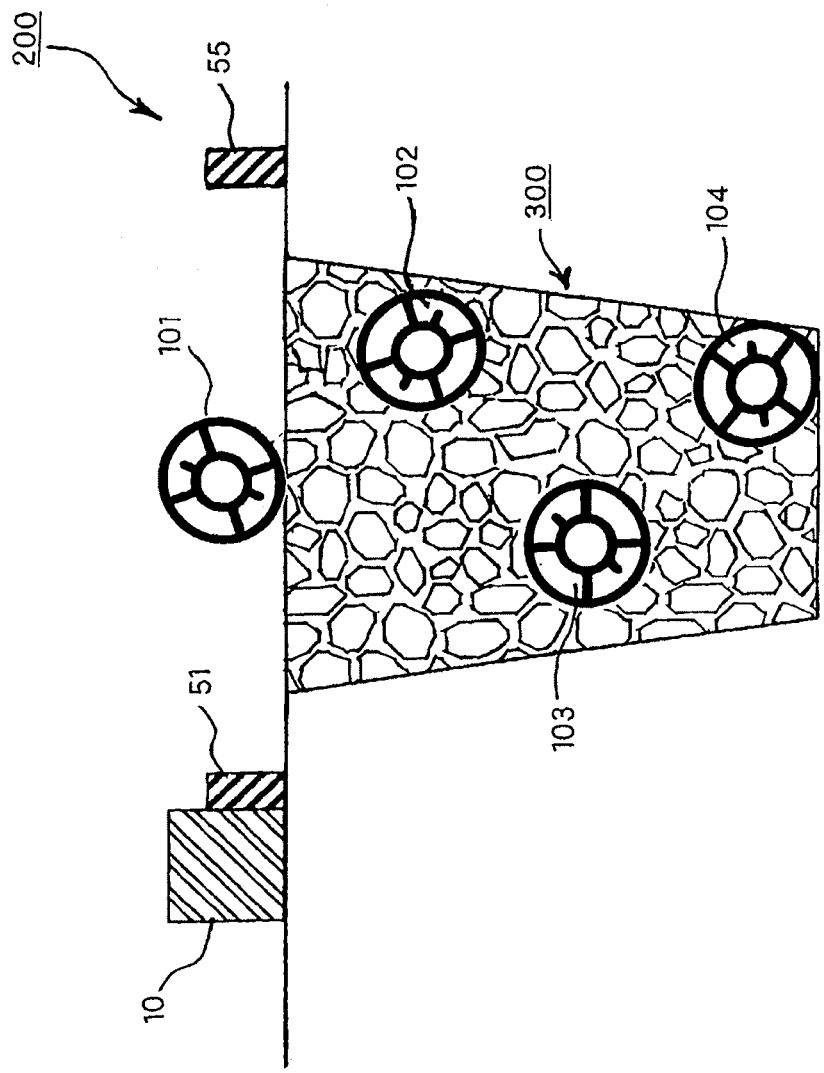
FIG. 7 is a longitudinal sectional view of the basic configuration of the ground control apparatus.

FIG. 6A is a plan view showing a basic configuration of the ground control apparatus, and FIG. 7 is a longitudinal sectional view of its basic configuration. In FIGS. 6 and 7, in the ground control apparatus 200, the sending vibrator 10 for controlling each of the pseudo rocks 100 (101 to 104 of FIG. 7), and plural receiving sensors 50 (51 to 59 of FIG. 6A) including acceleration sensors or vibration sensors are installed so as to surround a mineral deposit 300.

A personal computer PC (FIG. 6B) controls the receiving sensors 50 (51 to 59 of FIG. 6A) and the sending vibrator 10, and the personal computer PC has a program for control and by this program, for example, the sending vibrator 10 is controlled to send signals to the pseudo rocks 101 to 104 (FIG. 7) and the signals from the pseudo rocks 101 to 104 are received by the receiving sensors 50 and positions of the pseudo rocks 101 to 104 are pinpointed from analysis by a data analyzer 71 of the contents of the received signals and a difference between arrival times of the signals of each of the receiving sensors 51 to 59 (FIG. 6A).

The pseudo rocks 100 (four rocks 101 to 104 in FIG. 7) are installed and buried at measurement points of the inside of the mineral deposit 300, and it is difficult to communicate with the ground by a wireless system depending on a component or the density of rocks of the inside of the mineral deposit. Hence, vibration propagation-based communication with the ground control apparatus 200 is utilized using the vibration generator 5 and each of the strain gauges 9 housed in the inner shell sphere 2 (FIG. 1A) present in the pseudo rock 100 (FIG. 1A).

That is, the vibration generator 5 of each of the pseudo rocks 100 performs as a sender to the ground control apparatus 200, and the three-axis acceleration sensor 3 also performs as a receiver for receiving vibration sent from the ground control apparatus 200.

In addition, in the embodiment, the three-axis acceleration sensor 3 is combined as the receiver for receiving vibration sent from the ground control apparatus, but a dedicated acceleration sensor may be installed.

On the other hand, as shown in FIGS. 6 and 7, the sending vibrator 10 for controlling each of the pseudo rocks 100 (101 to 104) and the receiving sensors 50 (51 to 59 in FIG. 6A) are installed in the ground control apparatus 200. The plural receiving sensors 50 (eight receiving sensors 51 to 58 at a distance of 45° in the illustrated example) are preferably arranged around the mineral deposit and one receiving sensor 59 is arranged in the center of the mineral deposit from the standpoint of improvement in sensitivity.

Figures 8A, 8B:
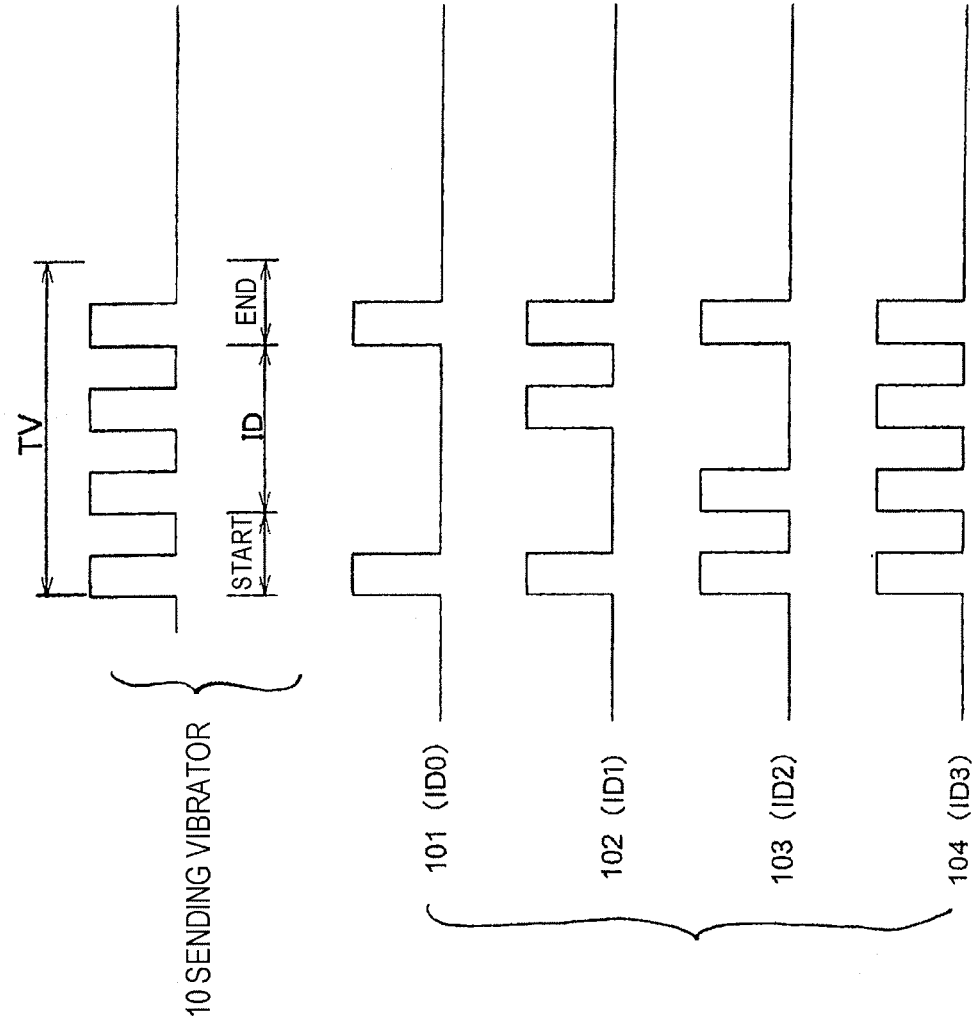
FIG. 8A shows four vibration pulses delivered by a sending vibrator of the ground control apparatus.
FIG. 8B shows vibration pulses showing separate IDs respectively included by four pseudo rocks.

Each of the pseudo rocks 100 includes an individual ID, respectively. In FIGS. 8A and 8B, for example, when four pseudo rocks 101 to 104 are used as shown in FIG. 8B, the sending vibrator 10 (FIG. 7) of the ground control apparatus 200 triggers each of the pseudo rocks during a period of time (TV) corresponding to four vibration pulses having start and end vibration pulses and two vibration pulses between the start and end vibration pulses as shown in FIG. 8A.

That is, an ID of a vibration pattern of (1, 0, 0, 1) with no vibration pulse between the start and the end is allocated to the pseudo rock 101 of ID0 and similarly, IDs of (1, 0, 1, 1), (1, 1, 0, 1) and (1, 1, 1, 1) are respectively allocated to the pseudo rocks 102 to 104 of ID1 to ID3.

Consequently, each of the pseudo rocks 101 to 104 identifies its own ID vibration pulse by a pattern of a vibration pulse for a period of TV described below sent from the sending vibrator 10 of the ground control apparatus 200, and individually activates each of the ECUs 7 (FIG. 4) from a standby state. And, each of the pseudo rocks 101 to 104 sends detected values etc. of the three-axis acceleration sensor 3, the three-axis geomagnetic sensor 4, the temperature sensor 6 and each of the strain gauges 9 together with respective ID vibration pulses to the ground control apparatus 200 through the vibration generator 5 to establish vibration propagation-based data communication.

FIGS. 9A to 9C show actuation of the sending vibrator 10 (FIG. 8A) installed in the same place as the first receiving sensor 51 (FIG. 6A) of the receiving sensors 50 in the ground control apparatus 200 and a situation in which vibration-based communication with the pseudo rock 104 (FIG. 8B) of ID3 is established, and when the ground control apparatus 200 sends an ID vibration pulse 91 of (1, 1, 1, 1) shown in FIG. 9A by the sending vibrator 10 for a period of TV, the pseudo rock 104 (FIG. 8B) of ID3 detects its own ID vibration pulse 92 by the three-axis acceleration sensor 3 (FIG. 1A) housed inside the pseudo rock 104 after Δt1 as shown in FIG. 9B.

The pseudo rock 104 receiving ID3 which is its own ID vibration pulse turns on a power source by power source control means 45 included by the ECU 7, and returns a vibration pulse 93 of ID3 which is its own ID to the ground control apparatus 200 by the vibration generator 5 (FIG. 1A) housed inside the pseudo rock 104 as shown in FIG. 9C and thereafter, converts detected values of the three-axis acceleration sensor 3, the three-axis geomagnetic sensor 4, the temperature sensor 6, each of the strain gauges 9, etc. into corresponding vibration pulses from the next pulse train 94 and sequentially sends the vibration pulses to the ground control apparatus 200 by the vibration generator 5. In addition, one bit by vibration used herein corresponds to five seconds (described below).

FIG. 10A shows a data stream at the time when the pseudo rock 100 sends an ID vibration pulse and a detected value of each sensor to the ground control apparatus 200 by the vibration generator 5. In send data 80, as described in FIG. 8B, one bit is allocated at the time of start, and two bits are allocated for ID recognition for selecting a specific pseudo rock from among plural pseudo rocks, and one bit is allocated for start. Then, four bits are respectively allocated for inclination angles θx, θy, θz at which the X, Y, Z axes of the pseudo rock 100 described in FIG. 2 are respectively inclined to the vertical direction, and four bits are respectively allocated for angles θHx, θHy of inclination to the N-S direction of the pseudo rock 100 described in FIG. 3, and four bits are respectively allocated for stresses PX, PY, PZ of each of the strain gauges 9 for three directions of the X, Y, Z axes, and four bits are allocated for sensor output of the temperature sensor 6, and two bits are allocated for end. In addition, an inclination angle θHz can be obtained later by calculation, so that bits for the inclination angle θHz are not prepared. In addition, a three-dimensional coordinate analyzer 73 in the ground control apparatus 200 is configured to analyze an angle of inclination in a horizontal direction or an angle of inclination to a vertical direction of three-dimensional coordinates (X axis, Y axis, Z axis) of the pseudo rock 100 based on a detected value of each of the strain sensors 9 or the three-axis geomagnetic sensor 4 of the pseudo rock 100.

In one bit by vibration used herein, a configuration of one bit of FIG. 10B is made by vibration of an eccentric motor as enlarged and shown in FIG. 10C, and the one bit is constructed by collections of sine waves of about 60 Hz for about five seconds.

Figure 11:
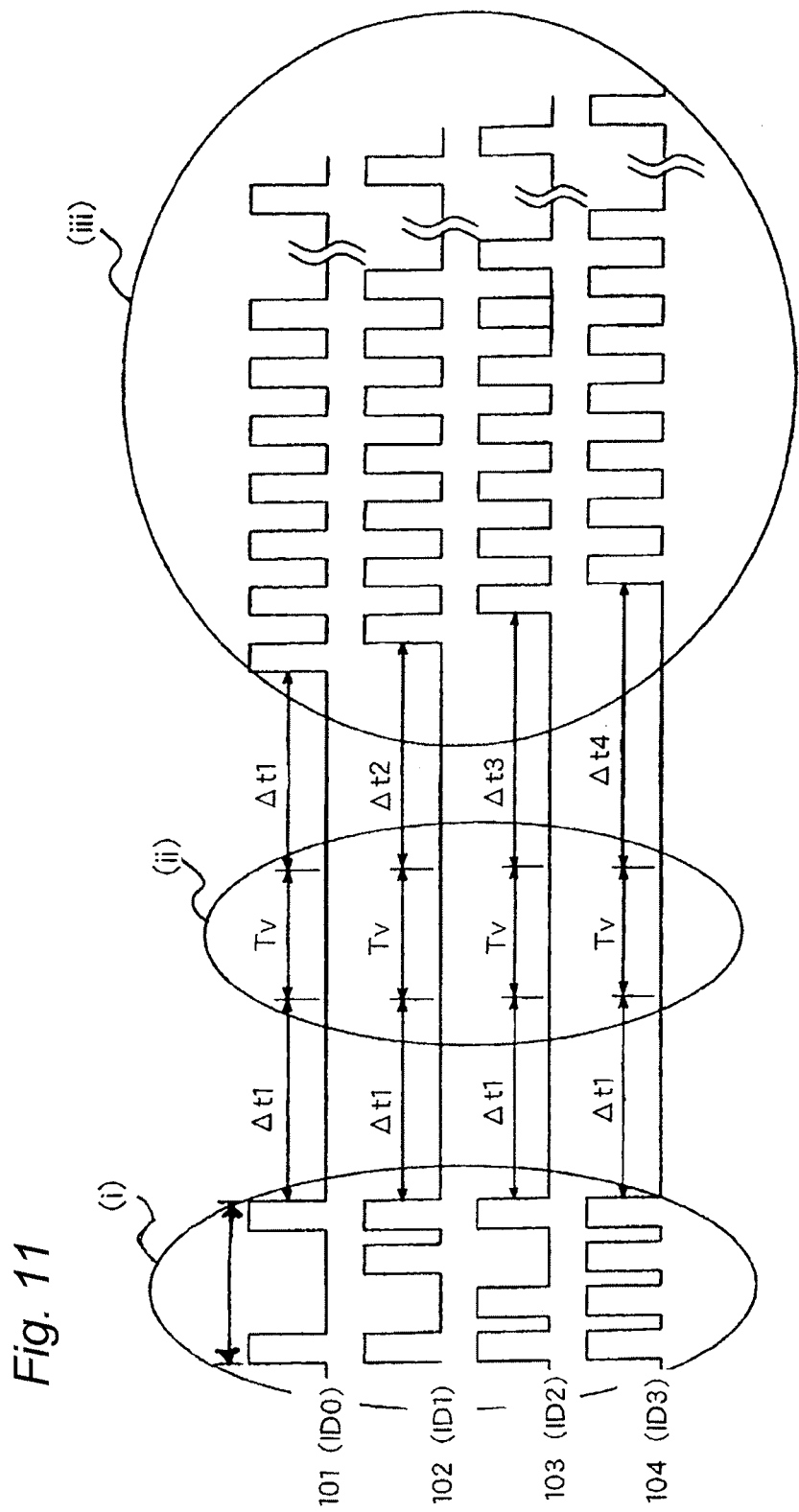
FIG. 11 is a diagram showing vibration-based data communication between plural pseudo rocks and the ground control apparatus.

FIG. 11 shows a situation as follows. The four pseudo rocks 101 to 104 of ID0 to ID3 are triggered in a section (i) by vibration generation of a start ID sent from the sending vibrator 10 of the ground control apparatus 200 and the respective three-axis acceleration sensors 3 (FIG. 1A) of the four pseudo rocks 101 to 104 receive in a section (ii) after Δt1 to Δt4, respectively. Further, respective ID vibration pulses and sensor detected values are generated by the vibration generator 5 (FIG. 1A) in a section (iii) after Δt1 to Δt4, respectively. Then, the receiving sensor 51 (FIG. 6A) formed in the same position as that of the sending vibrator 10 of the ground control apparatus 200 detects the pulses and the detected values.

In addition, vibrations of various frequencies and waveforms randomly occur with collapse etc. inside the mineral deposit 300 (FIG. 7), but the vibrations can be clearly distinguished from vibrations having a regular frequency used in communication between the individual pseudo rocks 101 to 104 and the ground control apparatus 200 as described above, so that the vibrations occurring inside the mineral deposit are not regarded as noise in principle.

In the case of expecting an influence of noise by other vibration sources etc., a malfunction due to the noise can be prevented more surely by repeating generation of ID vibration pulses from the ground control apparatus and response of ID vibration pulses from the corresponding pseudo rock plural times.

After vibration-based data communication is established, it is necessary to pinpoint three-dimensional coordinates of the pseudo rock inside the mineral deposit. As described previously, the plural receiving sensors 51 to 59 (FIG. 6A) are installed in the ground control apparatus and according to the three-dimensional coordinates of a specific pseudo rock inside the mineral deposit, linear distances between this pseudo rock and the receiving sensors differ.

Since vibration generally propagates at a constant speed inside a specific mineral deposit, as shown in FIG. 11, after a lapse of time (Δt1) necessary for each of the pseudo rocks 101 to 104 to receive its own ID vibration pulse in response to the ID vibration pulse from the sending vibrator 10 of the ground control apparatus 200 and time (Tv) necessary for the vibration generator 5 of each of the pseudo rocks 101 to 104 to complete receiving, times necessary to send its own ID signal pulse and a detected value of each sensor and for the receiving sensor 51 of the ground control apparatus 200 to receive the ID signal pulse and the detected value require Δt1 to Δt4, respectively.

Therefore, a value obtained by subtracting Δt1 and ΔTv from time necessary for each of the receiving sensors 51 to 59 of the ground control apparatus 200 to receive vibration by the vibration generator 5 of the corresponding pseudo rock from the instant that the sending vibrator 10 of the ground control apparatus 200 starts oscillation of the ID vibration pulse is proportional to a distance between each of the receiving sensors 51 to 58 and the subsequent pseudo rock.

Therefore, a position analyzer 72 of the ground control apparatus 200 can accurately pinpoint a three-dimensional position of the pseudo rock inside the mineral deposit by analyzing the receiving timing of at least three receiving sensors on the same principle as the GPS.

In addition, the above embodiment is constructed so that vibration-based communication between the pseudo rock and the ground control apparatus is established and direction or magnitude of a pressure, a stress or a shock force acting on the pseudo rock is analyzed by the ground control apparatus in real time, but after a detected value of each sensor is stored in the memory 42 (FIG. 4) of the ECU 7 (FIG. 4) inside of the pseudo rock together with measurement time and the pseudo rock is taken out, data recorded on this memory 42 can also be analyzed at the common time axis.

Figure 12:
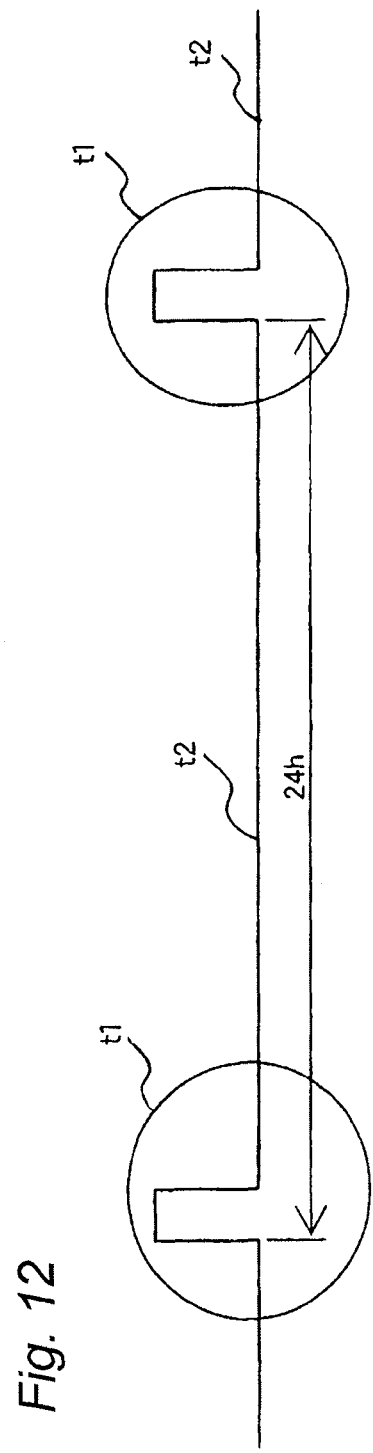
FIG. 12 is a diagram showing an example of a trigger in the case of making a measurement over a long period of time.

Also, in the case of measuring very slow collapse over a long period of time, a measurement is made in a section (t1) from the ground control apparatus 200, for example, once per 24 hours as shown in FIG. 12. That is, a starting signal is sent to each of the pseudo rocks and a detected value of each sensor is acquired. In a subsequent section (t2), a signal for turning off a power source of each of the pseudo rocks may be sent. Each of the pseudo rocks is controlled by a timer so as to be activated for about 30 minutes per 24 hours. The ground control apparatus 200 is always in a standby state, and each of the pseudo rocks is activated for about 30 minutes per 24 hours by timer control to make the measurement. Thus, in the pseudo rock, only a timer circuit is operated and when necessary, a power source is supplied to a main substrate and thereby, a lower-power-consumption power source circuit can be constructed.

The present application is based on Japanese patent application No. 2010-176677 filed on Aug. 5, 2010, and the contents of the patent application are hereby incorporated by way of reference.

INDUSTRIAL APPLICABILITY

According to the invention as described above, a pseudo rock having an average shape and size constituting a mineral deposit or ground is arranged inside the mineral deposit or the ground, and vibration propagation-based communication between this pseudo rock and a ground control apparatus is established and thereby, a stress applied from other rocks etc. before or after the start of collapse or before or after the occurrence of a liquefaction phenomenon, or behavior associated with the stress can accurately be measured from the pseudo rock buried inside the mineral deposit or the ground difficult to establish communication using a wireless system etc.

By using this measured value, timing of the start of collapse at the time of mining adopting a block caving method, magnitude of the collapse or a mechanism of the occurrence of the liquefaction phenomenon at the time of the occurrence of the liquefaction phenomenon can be simulated with high accuracy, and the invention is expected to be widely used in safety measures, disaster-prevention measures, etc. at a mining site.

REFERENCE SIGNS LIST

1 OUTER SHELL SPHERE (PRESSURE OUTER WALL)
2 INNER SHELL SPHERE
3 THREE-AXIS ACCELERATION SENSOR
4 THREE-AXIS GEOMAGNETIC SENSOR
5 VIBRATION GENERATOR (VIBRATOR)
6 TEMPERATURE SENSOR
7 ELECTRIC CONTROL UNIT (ECU)
8 COLUMNAR MEMBER
9 STRAIN GAUGE
10 SENDING VIBRATOR
11 BATTERY SPACE
41 ANALOG-TO-DIGITAL (A/D) CONVERTER
42 MEMORY
43 CPU
44 BATTERY
45 POWER SOURCE CONTROLLER
48 TRANSISTOR
48B BASE
50,51~59 RECEIVING SENSOR
71 DATA ANALYZER
73 POSITION ANALYZER
73 THREE-DIMENSIONAL COORDINATE ANALYZER
100,101~104 PSEUDO ROCK ACCORDING TO THE PRESENT EMBODIMENT
200 GROUND CONTROL APPARATUS
300 MINERAL DEPOSIT

The invention claimed is:

1. A pseudo rock, configured to be buried inside a mineral deposit or under ground, comprising:
a housing having an average shape and size of rocks existing inside the mineral deposit or the ground;
a plurality of strain sensors provided in the housing and configured to detect a stress acting in positive and negative directions of each axis with respect to three-dimensional coordinates (X axis, Y axis, Z axis);
a three-axis acceleration sensor provided in the housing and configured to detect acceleration acting in each axis of the three-dimensional coordinates;
a vibration generator provided in the housing and configured to produce vibration in a specific direction with respect to the three-dimensional coordinates; and
a controller provided in the housing and configured to convert respective detected values of the strain sensors and the three-axis acceleration sensor into vibration pulses of specific patterns and outputting the vibration pulses to the vibration generator.

2. The pseudo rock according to claim 1, wherein
the controller is configured to output the vibration pulses of the specific patterns corresponding to the detected values of the strain sensors and the three-axis acceleration sensor together with an ID vibration pulse, which is individually allocated to the pseudo rock, to the vibration generator.

3. The pseudo rock according to claim 2, wherein
the controller includes a power source controller configured to turn on an own power source when the three-axis acceleration sensor or a vibration sensor individually provided detects vibration of the ID vibration pulse.

4. The pseudo rock according to claim 1, further comprising:
a three-axis geomagnetic sensor provided in the housing.

5. A ground control apparatus on ground, configured to control a pseudo rock configured to be buried inside a mineral deposit or under ground, including: a housing having an average shape and size of rocks existing inside the mineral deposit or the ground; a plurality of strain sensors provided in the housing and configured to detect a stress acting in positive and negative directions of each axis with respect to three-dimensional coordinates (X axis, Y axis, Z axis); a three-axis acceleration sensor provided in the housing and configured to detect acceleration acting in each axis of the three-dimensional coordinates; a vibration generator provided in the housing and configured to produce vibration in a specific direction with respect to the three-dimensional coordinates; and a controller provided in the housing and configured to convert respective detected values of the strain sensors and the three-axis acceleration sensor into vibration pulses of specific patterns and outputting the vibration pulses to the vibration generator,
the ground control apparatus comprising:
a sending vibrator configured to send an ID vibration pulse of the pseudo rock to the pseudo rock to trigger the pseudo rock; and
a receiving sensor configured to detect vibration from a vibration generator of the pseudo rock.

6. The ground control apparatus according to claim 5, wherein
the receiving sensor detects a vibration pulse corresponding to detected values of the strain sensors and the three-axis acceleration sensor together with vibration corresponding to an ID vibration pulse of the pseudo rock from the pseudo rock, and
the ground control apparatus further comprises a data analyzer configured to analyze each of the detected values of the strain sensors and the three-axis acceleration sensor of the pseudo rock together with the ID vibration pulse of the pseudo rock.

7. The ground control apparatus according to claim 6, wherein
the receiving sensor is arranged in at least three places of an outer periphery of the mineral deposit or the ground, and
the ground control apparatus further comprises a position analyzer configured to analyze a three-dimensional position of the pseudo rock inside the mineral deposit or the ground based on a difference between arrival times of signals from a vibration generator of the pseudo rock.

8. The ground control apparatus according to claim 6, further comprising:
a three-dimensional coordinate analyzer configured to analyze an angle of inclination in a horizontal direction or an angle of inclination to a vertical direction of three-dimensional coordinates (X axis, Y axis, Z axis) of the pseudo rock based on a detected value of each of the strain sensors or a three-axis geomagnetic sensor of the pseudo rock.

9. A rock behavior analysis system, configured to analyze a rock inside of a mineral deposit or under ground, comprising:
a pseudo rock, configured to be buried inside a mineral deposit or under ground, including:
a housing having an average shape and size of rocks existing inside the mineral deposit or the ground;
a plurality of strain sensors provided in the housing and configured to detect a stress acting in positive and negative directions of each axis with respect to three-dimensional coordinates (X axis, Y axis, Z axis);
a three-axis acceleration sensor provided in the housing and configured to detect acceleration acting in each axis of the three-dimensional coordinates;
a vibration generator provided in the housing and configured to produce vibration in a specific direction with respect to the three-dimensional coordinates; and
a controller provided in the housing and configured to convert respective detected values of the strain sensors and the three-axis acceleration sensor into vibration pulses of specific patterns and outputting the vibration pulses to the vibration generator; and
a ground control apparatus including:
a sending vibrator configured to send an ID vibration pulse of the pseudo rock to the pseudo rock to trigger the pseudo rock; and
a receiving sensor configured to detect vibration from the vibration generator of the pseudo rock.

* * * * *